United States Patent [19]

van de Moesdijk et al.

[11] 4,420,622

[45] Dec. 13, 1983

[54] PROCESS FOR THE PREPARATION OF A 5-ALKYL-BUTYROLACTONE

[75] Inventors: Cornelis G. M. van de Moesdijk, Elsloo; Petrus H. J. Janssen, Geleen, both of Netherlands

[73] Assignee: Stamicarbon B.V., Geleen, Netherlands

[21] Appl. No.: 380,757

[22] Filed: May 21, 1982

[30] Foreign Application Priority Data

Jul. 2, 1981 [NL] Netherlands .......................... 8103173

[51] Int. Cl.$^3$ ........................................... C07D 307/32
[52] U.S. Cl. ..................................... 549/326; 549/295
[58] Field of Search .......................................... 549/326

[56] References Cited

U.S. PATENT DOCUMENTS 2,786,852 3/1957 Dunlop et al. ...................... 549/326

FOREIGN PATENT DOCUMENTS 1013642 8/1957 Fed. Rep. of Germany .

Primary Examiner—Norma S. Milestone

[57] ABSTRACT

The preparation of 5-alkyl-butyrolactones is described using $C_8$ hydrocarbon levulinate esters, with side-chain alkyl substituents of up to 4 carbon atoms as starting material, with the reaction being conducted with hydrogen at a temperature of from 150° to 325° C., in the gas phase, and in the presence of a hydrogenation catalyst composed of metals of Group VIII or Group Ib of the Periodic Table. The process provides extremely high conversion rates and lactone yields, the prolonged catalyst activity.

5 Claims, No Drawings

PROCESS FOR THE PREPARATION OF A 5-ALKYL-BUTYROLACETONE

The invention relates to a process for the preparation of 5-alkyl-butyrolactone compounds.

From German patent specification No. 1,013,642 it is known that levulinic acid can be hydrogenated in the gas phase to 5-methyl-butyrolactone (γ-valerolactone), with the aid of a copper-containing catalyst. According to the disclosure of said German patent specification, a very high yield can be obtained in this process.

However, when this known process for the preparation of 5-methyl-butyrolactone or another 5-alkyl-butyrolactone by hydrogenation of levulinic acid or another 4-oxo-alkane carboxylic acid was repeated, it was observed that the lifetime of the catalyst was very short indeed. After a reaction time of 20 hours, for instance, the conversion of the acid is considerably lowered, and harmful, wasteful side reactions occurred to a considerable extent.

The present invention now provides a process for the preparation of a 5-alkyl-butyrolactone which avoids the above-described disadvantage.

The process provided by the present invention for the preparation of a 5-alkyl-butyrolactone is characterized by reacting a keto-ester with formula:

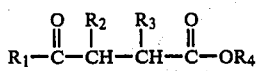

(wherein $R_1$ represents an alkyl group with 1-4 carbon atoms, $R_2$ and $R_3$ each independently represents hydrogen or an alkyl group with 1-4 carbon atoms, and $R_4$ represents a hydrocarbon group with at most 8 carbon atoms), with hydrogen, at a temperature of 150°-325° C., in the gas phase and in the presence of a hydrogenation catalyst, and recovering from the reaction mixture thus-obtained a 5-alkyl-butyrolactone which has the general formula

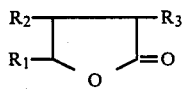

wherein $R_1$, $R_2$ and $R_3$ have the meaning indicated above.

As a by-product of this process according to the present invention, there is formed an alcohol with the general formula $R_4OH$, $R_4$ having the meaning indicated above. Such alcohol can be separated off from the reaction mixture by fractional distillation, and can be used, if desired, for the preparation, from the corresponding keto-acid, of additional keto-ester for further conversion according to this invention.

By preference, alkyl groups with at most 4 carbon atoms are used as the hydrocarbon group $R_4$. Other hydrocarbon groups, with at most 8 carbon atoms, including for example the groups cyclohexyl and benzyl, can also be used, but this does not result in any advantage.

The reaction according to this invention can be realized using known hydrogenation catalysts, for example catalysts containing a metal or a compound of a metal from Group VIII or Group Ib of the Periodic Table (Lange's Handbook of Chemistry, 12th Ed.). Very suitable catalysts are those containing nickel and/or cobalt in the form of metal and/or metal compound. The catalysts can be employed on a solid particulate support, such as, for instance, active carbon, graphite, silicon oxide, chromium oxide, aluminium oxide, magnesium oxide, zinc oxide and mixtures of these materials. The amount of supporting material can vary, for instance in such a way that the quantity of catalyst amounts to 0.5-20% by weight, preferably 1-10% by weight (calculated as metal and based on the total amount of catalyst material including the support).

The hydrogenation-catalysts which are used in the process according to the invention are already known in themselves and can be prepared for instance by treating the support with a salt of the concerning metal followed by reduction with hydrogen in the manner described on page 265 of Preparation C of Catalysts II by G. H. van den Berg and H. Th. Rynten (Elsevier Amsterdam 1979), the disclosure of which is incorporated herein by reference.

The process according to this invention can be realized at various temperatures within the range 150°-325° C. Advantageously, the temperature is chosen within the range 175°-275° C., because then a high conversion and a good yield can be achieved.

For the practical realization of the reaction according to this invention, the methods generally used for gas-phase reactions, already known as such, are suitable, for instance, the technique wherein the starting product in a gaseous state and, if desired, diluted with an inert gas such as nitrogen, is passed over a fixed bed catalyst together with hydrogen. The space velocity can be varied, for instance, between 0.01 and 2 grams of keto-ester per milliliter of catalyst material (bulk volume) per hour. The amount of hydrogen can also be varied, for example between 1 and 15 mol hydrogen per mol of keto-ester to be converted. It is also possible to use more than 15 mol hydrogen per mol of the keto-ester to be converted, but this does not result in any advantage.

By cooling the gaseous reaction mixture, a condensate can then be obtained, along with a hydrogen-containing gas which can be recycled. From the condensate the desired product can be recovered by, for instance, fractional distillation. It is also possible to recover the desired product from the condensate by extraction.

The compounds obtained according to the invention can be used for various purposes, for example in the flavors and fragrances industries.

This invention will now be further elucidated in the following non-limiting Examples.

EXAMPLE I

For approximately 60 hours, a gaseous mixture of hydrogen and ethyl levulinate is passed downward through a vertical tubular reactor (diameter 18 mm, length 400 mm) in which there is a zone of 25 ml (bulk volume) of catalyst. The catalyst zone is bonded on both sides by a zone of 25 ml of inert ceramic material particles. The catalyst employed in this Example is cobalt on a silica support of moderate porosity (internal surface 350-500 m² per gram, activated by passing hydrogen over it for 16 hours at 350° C.; 10% by weight of Co) and in the form of lumps with a diameter of 3-8 mm.

The gaseous mixture passed through (6 mol hydrogen per mol of ethyl ester) is obtained by evaporating the liquid ethyl ester and mixing the vapor with hydrogen. Per ml (bulk volume) of catalyst, 0.2 gram ethyl ester is passed through per hour. For the first 47 hours, the temperature of the catalyst is maintained at 200° C. with the aid of a heating jacket round the reactor, and afterwards at 250° C.

The composition of the reaction mixture is determined a number of times by leading the reaction mixture obtained through two series-arranged vessels which are cooled to 0° C. and −80° C. respectively, and then analyzing the condensed product thus-obtained by gas chromatography.

From this analysis, the weight of the amount of ester passed over the catalyst during the period of two hours and the weight of the amount of condensated product caught during this period, the conversion of the ester and the yield of lactone can be calculated.

By conversion herein is meant the amount of ester converted (the amount of ester passed over minus the amount of ester in the condensed product), expressed as a percentage of the amount of ester passed over. By lactone yield is meant the amount of lactone in the condensed product, expressed as a percentage of the amount of lactone which is theoretically possible to form from the amount of ester converted.

In the table below, the conversions and yields are presented, together with the operating time elapsed before the gaseous reaction mixture is passed through the cooled vessels for the 2-hour period.

TABLE

| | Example I | |
|---|---|---|
| Operating Time In Hours | Conversion % | Lactone Yield % |
| 21 | 99.7 | 99.5 |
| 45 | 98.8 | 99.5 |
| 48 | 97.9 | 99.5 |
| 55 | 92.6 | 99.5 |

When in place of the ester, levulinic acid itself is passed over the catalyst under identical conditions, after as little as 20 hours the conversion has dropped to 30% and the yield to 50%.

EXAMPLE II

In the manner described in Example I, a mixture of hydrogen and ethyl levulinate ester is passed over a copper-on-magnesium-oxide catalyst (38% by weight of Cu) in the form of tablets (diameter 5 mm, thickness 3 mm) for 5 hours. Per mol of ester 6 mol hydrogen are used. The temperature is maintained at 200° C., and the amount of ester passed over per ml of catalyst per hour is 0.2 gram.

After an operating time of 3 hours, the conversion and the lactone yield are determined as described in Example I, and are found to be 99.8% and 99.5% respectively.

EXAMPLE III

In the manner described in Example I, a mixture of ethyl levulinate ester and hydrogen is passed over a copper chromite catalyst (80% by weight of CuO, 20% by weight of $Cr_2O_3$) in the form of tablets (diameter 3 mm, thickness 3 mm), for 94 hours. Per mol of ethyl ester, 6 mol hydrogen is used per hour, the temperature being maintained at 200° C. The amount of ester passed over per ml of catalyst per hour is 0.2 gram.

The results found and the operating time are presented in the table below.

TABLE

| | Example III | |
|---|---|---|
| Operating Time In Hours | Conversion In % | Yield In % |
| 3 | 99.4 | 99.0 |
| 24 | 99.9 | 98.5 |
| 48 | 99.8 | 99.6 |
| 68 | 99.5 | 98.4 |
| 92 | 99.7 | 98.5 |

When, in place of the ester, levulinic acid itself is passed over the catalyst in the same manner, after an operating time of only 24 hours the conversion is observed to have dropped to 23% and the yield to 22.5%.

EXAMPLE IV

In the manner described in Example I, a mixture of hydrogen and 1,2-dimethyl-3-oxobutane-1-carboxylic acid methyl-ester is passed over a copper chromite catalyst (80% by weight of CuO and 20% by weight of $Cr_2O_3$) in the form of tablets (diameter 3 mm, thickness 3 mm) for 7 hours. Per mol of ester, 6 mol of hydrogen is used. The temperature is maintained at 230° C., and per ml of catalyst 0.2 g ester is passed over per hour.

After 5 hours, the conversion of the ester and the yield of 3,4,5-trimethyl-butyrolactone is determined as described in Example I. These were 99% and 89%, respectively.

EXAMPLE V

In the manner described in Example I, a mixture of hydrogen and ethyl levulinate ester is passed over a nickel-on-silicon-oxide catalyst (10% by weight of Ni, Houdry type H 1170) in the form of lumps with a diameter of 3 to 5 mm, for 6 hours. Per mol of ester, 6 mol hydrogen is used, and the temperature is maintained at 220° C. Per ml of catalyst, 0.2 g ester is passed over per hour.

After an operating time of 4 hours, the conversion and the lactone yield are determined in the same manner. These are 99.5% and 99%, respectively.

EXAMPLE VI

In the manner described in Example I, a mixture of hydrogen and methyl levulinate ester is passed over a nickel-on-silicon-oxide catalyst (10% by weight of Ni, Houdry type H 1170) in the form of lumps with a diameter of 3 to 5 mm, for 7 hours. Per mol of ester, 6 mol hydrogen is used. Per ml of catalyst, 0.2 g ester is passed over per hour, and the temperature is maintained at 220° C.

After an operating time of 5 hours, the conversion and the lactone yield are determined in the manner described. These are 99% and 98.5%, respectively.

The techniques employed in the foregoing Examples can be similarly employed with other alkyl levulinates within the scope of the above formula, and with other catalyst systems within the scope of the foregoing description with comparable results of sustained high conversions and high yields.

Accordingly, this invention is limited only by the spirit of the terms of the following claims.

What is claimed is:
1. A process for the preparation of a 5-alkyl-butyrolactone compound comprising reacting a ketoester of the formula

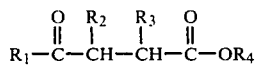

wherein $R_1$ represents an alkyl group of 1–4 carbon atoms, $R_2$ and $R_3$ each independently represent hydrogen or an alkyl group of 1–4 carbon atoms and $R_4$ represents a hydrogen group having at most 8 carbon atoms, with hydrogen at a temperature of 150°–325° C., in the gas phase and in the presence of a solid particulate hydrogenation catalyst, containing a metal or a compound of a metal from Group VIII or Group Ib of the Periodic Table, and recovering from the reaction mixture obtained a 5-alkyl-butyrolactone which has the general formula

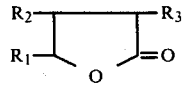

where $R_1$, $R_2$ and $R_3$ have the meaning indicated above.

2. Process according to claim 1, wherein said catalyst contains nickel and/or cobalt in the form of metal and/or metal compound.

3. Process according to either one of claims 1 or 2, wherein said temperature is 175°–275° C.

4. Process according to either one of claims 1 or 2, wherein said catalyst is used in the form of a fixed bed, and the reaction is conducted at a space velocity of 0.01–2 gram keto-ester per ml catalyst material per hour.

5. Process according to either one of claims 1 or 2, wherein said $R_4$ group represents an alkyl group with at most 4 carbon atoms.

* * * * *